United States Patent
Weissgerber (10) Patent No.: US 9,354,208 B2
(45) Date of Patent: May 31, 2016

(54) APPARATUS FOR GENERATING SMALL FLOW RATES IN A CHANNEL

(75) Inventor: Hans-Georg Weissgerber, Straubenhardt (DE)

(73) Assignee: Agilent Technologies, Inc., Santa Clara, CA (US)

( * ) Notice: Subject to any disclaimer, the term of this patent is extended or adjusted under 35 U.S.C. 154(b) by 1348 days.

(21) Appl. No.: 13/145,983

(22) PCT Filed: Jan. 22, 2009

(86) PCT No.: PCT/EP2009/050704
§ 371 (c)(1),
(2), (4) Date: Sep. 1, 2011

(87) PCT Pub. No.: WO2010/083884
PCT Pub. Date: Jul. 29, 2010

(65) Prior Publication Data
US 2011/0308325 A1 Dec. 22, 2011

(51) Int. Cl.
*G01F 1/00* (2006.01)
*G01N 30/10* (2006.01)
*G01N 30/32* (2006.01)
*G01N 30/60* (2006.01)

(52) U.S. Cl.
CPC .............. *G01N 30/10* (2013.01); *G01N 30/32* (2013.01); *G01N 30/6095* (2013.01)

(58) Field of Classification Search
CPC .............. G01F 7/00; G01F 1/00; G01N 1/00; G01M 3/04; B01D 15/08
USPC .................. 73/861, 61.56, 40, 195; 210/659
See application file for complete search history.

(56) References Cited

U.S. PATENT DOCUMENTS

| | | | | |
|---|---|---|---|---|
| 4,351,189 A * | 9/1982 | Gray | ........................ | G01F 1/58 137/101.19 |
| 5,323,657 A * | 6/1994 | Vander Heyden | ........ | G01F 1/48 374/36 |
| 5,859,356 A * | 1/1999 | Scheppers | ................ | G01N 1/26 73/1.07 |
| 5,938,932 A * | 8/1999 | Connelly | ............... | G01N 30/82 210/198.2 |
| 6,627,075 B1 | 9/2003 | Weissgerber et al. | | |
| 6,637,263 B2 * | 10/2003 | Zimmermann | ........ | G01F 1/684 73/195 |
| 6,712,085 B2 * | 3/2004 | Weissgerber | .......... | G01N 30/36 137/12 |
| 7,186,336 B2 * | 3/2007 | Gerhardt | ................ | G01F 1/363 210/101 |
| 7,250,138 B2 * | 7/2007 | Wick | ................... | G10N 15/065 422/50 |

(Continued)

FOREIGN PATENT DOCUMENTS

| | | |
|---|---|---|
| EP | 0495255 A1 | 7/1992 |
| EP | 1248096 A1 | 10/2002 |
| WO | 2004002878 A2 | 1/2004 |
| WO | 2004013578 A2 | 2/2004 |

OTHER PUBLICATIONS

EO Office Action mailed Jan. 11, 2013 for application No. 09 778 972.1.

(Continued)

*Primary Examiner* — Jewel V Thompson (57) ABSTRACT

A fluidic apparatus for a sample separation system includes a fluid inlet path for supplying a fluid, an inlet sensor adapted for measuring a flow rate of the fluid in the fluid inlet path, a splitting point arranged downstream of the fluid inlet path and adapted for splitting the fluid into a first path and into a second path, and a second path sensor adapted for measuring a flow rate of a part of the fluid conducted into the second path.

17 Claims, 5 Drawing Sheets

(56) References Cited

U.S. PATENT DOCUMENTS

| | | | | |
|---|---|---|---|---|
| 7,332,087 B2* | 2/2008 | Gerhardt | ............... | G01F 1/363 210/101 |
| 7,454,959 B2* | 11/2008 | Ruegenberg | ........... | G01N 30/32 73/61.56 |
| 7,955,843 B2* | 6/2011 | Barringer, Jr. | ....... | B01D 61/142 137/240 |
| 2005/0109698 A1 | 5/2005 | Gerhardt et al. | | |

OTHER PUBLICATIONS

International Search Report dated Jul. 9, 2009.
Zeng et al: "Parallel supercritical fluid chromatography/mass spectrometry system for high-throughput enantioselective optimization and separation" Journal of Chromatography, Elsevier Science Publishers B.V. Amsterdam, NL, vol. 1169, No. 1-2, Oct. 4, 2007, pp. 193-204, XP022284766, ISSN: 0021-9673, figure 1.

* cited by examiner

APPARATUS FOR GENERATING SMALL FLOW RATES IN A CHANNEL

This application is the National Stage of International Application No. PCT/EP2009/050704, filed on 22 Jan. 2009 which designated the United States of America, and was published as Publication No. WO 2010/083884 A1.

BACKGROUND ART

The present invention relates to a fluidic apparatus.

In liquid chromatography, a fluidic sample and an eluent (liquid mobile phase) may be pumped through conduits and a column in which separation of sample components takes place. The column may comprise a material which is capable of separating different components of the fluidic analyte. Such material, so-called beads which may comprise silica gel, may be filled into a column tube which may be connected to other elements (like a control unit, containers including sample and/or buffers) by conduits.

When the internal diameter of a column is small the requested amount of fluidic flow pumped through a fluidic conduit gets very low and precise operation of the fluidic system may be difficult.

U.S. Pat. No. 6,627,075 by the same applicant Agilent Technologies discloses that volume flows of liquids in capillary tubes of chromatographic separation columns for analytical liquid measuring technology are controlled. The volume flows are derived from a liquid transport, i.e. pump arrangement, which transports a total flow to a flow splitter that divides the total flow into an excess flow in an excess path and a working flow in a working path. A controller for the working flow responds to at least one working sensor. The working sensor senses the mass flow rate of the working flow and/or the pressure in the working path which is coupled with the working sensor or the pressure differential in conduits for the excess and working flows.

U.S. Pat. No. 7,186,336 discloses a method and an apparatus for monitoring and controlling the nano-scale flow rate of fluid in the operating flow path of a HPLC system. A first flow sensor is disposed in a first flow path between a first flow-divider and a fluidic tee. A second flow sensor is disposed in a second flow path between a second flow-divider and the fluidic tee. A first recycle flow restrictor is disposed in the first recycle flow path in fluid communication with the first flow-divider. A second recycle flow restrictor is disposed in the second recycle flow path. The permeability of each recycle flow restrictor can be selected to produce a desired flow rate with each respective flow path. The output signals of the first and second flow sensors control output of a pump within each flow path.

However, the precise control of very small fluidic flows may be difficult, since pumps may be not easily scalable and adapted for delivering very small volumes.

DISCLOSURE

It is an object of the invention to provide an efficient fluidic apparatus capable of operating at small fluidic flow rates. The object is solved by the independent claims. Further embodiments are shown by the dependent claims.

According to an exemplary embodiment of the present invention, a fluidic apparatus for a sample separation system (such as a liquid chromatography system) is provided comprising a fluid inlet path (which may comprise capillaries or other fluidic conduits) for supplying a fluid (which may have multiple separate fluidic components), an inlet sensor (for instance for quantifying fluid movements in terms of volumetric or mass flow rates) adapted for measuring a flow rate of the fluid (for instance separately for different components of the fluid) in the fluid inlet path, a splitting point (such as a fluidic tee) arranged downstream the fluid inlet path and adapted for splitting the fluid into a first path and into a second path (which may comprise capillaries or other fluidic conduits), and a second path sensor (for instance for quantifying fluid movements in terms of volumetric or mass flow rates) adapted for measuring a flow rate of a part of the fluid (for instance of a mixture of multiple fluid components) conducted into the second path.

According to another exemplary embodiment, a method of handling a fluid in a sample separation system is provided, wherein the method comprises supplying the fluid to a fluid inlet path, measuring a flow rate of the fluid in the fluid inlet path, splitting the fluid downstream the fluid inlet path into a first path and into a second path, and measuring a flow rate of a part of the fluid conducted into the second path.

In an embodiment, a measurement signal of an upstream sensor may be used as a basis for controlling a pump pumping the fluid through the fluidic system. A measurement signal of a downstream sensor may be used as a basis for controlling a splitting mode (such as adjusting a splitting ratio) according to which a volume of the fluid is partitioned into two paths, for instance a waste path and a column path. Depending on requirements of a specific application, operation of the system may be based on only a part of the system's components and other parts may be selectively deactivated (for instance, the system may be driven in a splitting mode or in a splitless mode), to thereby increase the flexibility for an operator. Operation of upstream sensor and downstream sensor may be coordinated and their measurement signals may be considered in combination to obtain a smart fluid control system being operable to meet requirements over a broad range of flow rates, including very small flow rates.

The provision of a variable splitting option allows to adjust a splitting ratio (based on a measurement signal of a sensor downstream the mixing point) according to which the fluid is splitable downstream the fluid inlet path. Consequently, fluid may be provided in a conveniently large quantity within the fluid inlet path which relaxes the requirements regarding performance and resolution of a pump, an inlet path sensor, etc. in the fluid inlet path. In other words, combining a splitting opportunity at a downstream position with a sensor comprising fluid inlet path upstream thereof may allow to use relatively simple and hence cheap components. In addition, the provision of a sensor in the fluid inlet path may simultaneously allow for a precise control of the pumping performance in the fluid inlet path. Advantageously, pump control and splitting ratio control may be integrated in a single control entity and may therefore be synchronized, if required or desired. Moreover, the dynamic range (particularly a range of fluid flow which can be served by the fluidic device) of the fluidic device may be very large, since the splitting function may be selectively switched on or off. For example, a large flow rate may be accomplished by disabling a splitting function and actively controlling only the fluid inlet path. For example, a small flow rate may be accomplished by enabling a splitting function in addition to an active control of the fluid inlet path. Thus, the range of fluid volume per time deliverable by the fluidic apparatus may be very large.

In the following, further exemplary embodiments of the fluidic apparatus will be explained. However, these embodiments also apply to the method.

Exemplary embodiments are related to a concept for low flow solvent generation. In such a system, several measuring devices (for instance flow sensors) may be used.

In one embodiment, a chromatographic pump may be used to deliver flow in two channels. A flow sensor may measure and control the delivered solvent in the individual channels. The solvents may be mixed afterwards. After the mixing point, the total flow rate may be determined by a further flow sensor. This sensor may measure the amount of mixed solvents needed at the apparatus outlet for a chromatographic column. This sensor may be called a "nano flow sensor".

Also adapted in the mixing point or afterwards is a splitting point. In the splitting point a channel may be provided which guides solvent to a selector for selecting a fluid flow mode. With this selector, a hydraulic restrictor can be selected out of a variety of different restrictors, or the channel can be flushed (which may be denoted as a purge mode) or blocked completely (which may be denoted as a blank nut mode). The hydraulic restrictor can be a fixed or a variable restrictor.

The flow rate before the splitting point may be denoted as a primary flow rate. The flow rate after the splitting point into direction apparatus outlet onto the chromatographic system may be denoted as used flow rate or column flow rate. The flow rate towards the restrictors may be named waste flow rate.

Such a system may offer the possibility to operate the pump in a direct mode. In such a direct mode, the selector may be positioned to plug the outlet of the waste flow. All solvent delivered from the pump may be mixed and delivered to the outlet onto the chromatographic column. The inlet flow sensors in the individual channels determine the composition and the sensor in the outlet path measure the column flow rate.

Such a system offers the possibility to operate the apparatus in an actively controlled split mode: The totally delivered flow into the apparatus may be only partially delivered to the apparatus outlet onto the chromatographic system. Depending on the restrictor, a portion of the liquid may be delivered into the waste channel. The delivered amount of solvent into the outlet port may be measured by the outlet flow sensor. The pump itself may be regulated to compensate for column flow variations.

It is possible to switch between both modes in accordance with application performance needs. The pump performance of delivering precise flow rates and solvent compositions can get worse with decreasing flow rate. Therefore, a split mode may be advantageous for proper performance especially at very small flow rates. On the other hand, the direct delivering mode may be still good enough for instance for flushing systems, delivering sample onto an enrichment column or to condition a column prior to an application, etc.

It may be possible to operate the pump in the split mode at low primary flow rate. The output of the individual channels may be measured and regulated. Thus leaks in individual channels can be controlled and compensated. A broad flow rate range may be possible: The synergetic combination of split flow and direct flow concepts may offer a wide range of flow rates.

It may be possible to integrate a mixer device in between the mixing and split point. Homogenous mixing of fluids from several channels may be advantageous for precise and reliable separation results. If the apparatus is operated in the split mode, the volume of the mixing device can be flushed with the primary flow rate which is usually higher compared to the apparatus outlet flow rate. Therefore, the total flush time can be kept short and the productivity may be increased.

With exemplary embodiments, the needs for the dynamic range (i.e. an operating range of flow rates with which a sensor may works properly) of the flow sensors may be reduced. The primary flow rates can be reduced or minimized in a split mode (i.e. when reducing a flow rate in individual channels by splitting a flow over multiple channels). It is possible to perform a calibration of sensors in the apparatus unit. Compensation of leaks in individual pump channels may be possible. It may be possible to avoid channel cross-flow if several channels are in use (i.e. undesired flow of a fluid from one channel into another one). Fixed restrictors (i.e. restrictors having a fixed extent of restriction) may be combined with a variable primary flow rate. Constant primary flow rate may be combined with a variable restrictor (i.e. a restrictor having a modifiable extent of restriction).

In an embodiment, the first path may be a waste path adapted for guiding a part of the fluid towards a waste. The term "waste" may particularly denote a container in which fluid from the first path can be collected for disposal or further processing or further use. However, in an embodiment, fluid conveyed into the waste path is not used any more for performing a sample separation. By adjusting a ratio of fluid being conducted into the waste path, an indirect control of fluid being conducted in the other parallel second path may be possible. A large portion of fluid being conducted into the waste path from the total delivered primary flow rate may correspond to an operation mode in which extremely small fluid volumes are conducted into the second path onto the chromatographic column. Thus, the provision of a waste path may allow for an operation of a sample separation system with very small fluid volumes. Thus sample separation systems are e.g. called 'nano flow separation systems'.

The second path may be a use path (such as a column path) adapted for guiding a part of the fluid (if the apparatus is operated in split mode) towards a processing unit (such as a separation column) using the part of the fluid for a processing application (such as a chromatographic sample separation). Such a processing unit may be a sample separation unit like a chromatographic column. Therefore, by splitting the fluid into the waste part and into the use path, a ratio of used fluid may be adjusted so that a handling of very small flow rates is enabled. Therefore, the term "use path" may particularly denote a path into which fluid is conducted which is used for sample separation purposes. For example, two or more fluidic components (such as water and an organic solvent) may be supplied separately in the fluid inlet path and may be mixed at a mixing point. Optionally both fluidic components are mixed in a mixing unit. Fluid from the fluid inlet path may be splitted or separated into a use path for further use of the corresponding fluid as a mobile phase for separating a sample to be conducted through a chromatographic column, and into a waste path. In an alternative embodiment, it is also possible that the fluid in the first path is used for any useful purpose, or is recycled.

In an embodiment, the fluid inlet path may comprise a first inlet conduit for supplying a first fluidic component (such as water) of the fluid, may comprise a second inlet conduit for supplying a second fluidic component (such as an organic solvent like acetonitrile, ACN) of the fluid, and may comprise a mixing point for mixing the first fluidic component with the second fluidic component upstream the splitting point. Thus, two or more different fluidic components may be mixed in accordance with a specific composition ratio which can be changed over time by controlling corresponding fluid pump channels, for instance to provide a gradient of a fluid composition in the scenario of a chromatographic separation application.

Proper mixing of the various fluidic components can be promoted by a dedicated mixing unit (for instance arranged between the mixing point and the splitting point) and being adapted for actively promoting mixture of the first fluidic component and the second fluidic component. For example, such a mixture may be promoted efficiently by a curvature of a fluidic channel through which the fluidic mixture is conducted.

The inlet sensor may be adapted for measuring a flow rate of the first fluidic component of the fluid. Additionally or alternatively, the inlet sensor may also be adapted for measuring a flow rate of the second fluidic component of the fluid. In an embodiment, a separate sensor may be located in each of the fluidic conduits transporting the first fluidic component and the second fluidic component of the fluid.

Particularly in the scenario of a liquid chromatography experiment, a ratio between the flow rate of the first fluidic component and the flow rate of the second fluidic component may be adjustable for adjusting a composition of the fluid, particularly for adjusting composition of the fluid in a time-dependent manner. When fractions of a fluidic sample such as a biological sample has been trapped on a chromatographic column, separation of this sample can be effected by providing a solvent with a variable concentration of multiple constituents to generate a fluid gradient. By taking this approach, different fractions of the sample trapped on the chromatographic column may be selectively released from the column and may be detected fraction-wise as separated fractions, for instance using an optical detector. Therefore, the system may be capable of varying the ratio of the two or more fluidic components over time.

The fluidic apparatus may comprise a pump for pumping the fluid through the fluid inlet path. Such a pump may be a piston pump. It is possible that a separate pump is provided for each fluid channel of the inlet path. When a sensor upstream the splitting point in the fluid inlet path measures one or more flow rates of the fluidic components, operation of the pump may be controlled by a feedback signal received from the sensors. Control of the pump or pumps may be in accordance with a mixing ratio, a total flow rate of the fluid, etc.

In an embodiment, the pump may be adapted for pumping the fluid onto the chromatographic column with a flow rate in a range between about 0.05 µl/min and about 500 µl/min. Such a flow rate may be adjustable by a user. The combination of a splitting and direct delivering architecture may allow to obtain such a high dynamic range.

The pump may be adapted for pumping the fluid through the second flow path towards a sample separation unit (such as a chromatographic column) with a flow rate in the second flow path in a range between about 0.01 µl/min and about 500 µl/min, particularly in a range between about 0.05 µl/min and about 100 µl/min. These flow rates may be total flow rates flowing through a separation column. Without a splitting mode, such flow rates (particularly at the lower end of the given ranges) may involve high requirements regarding performance of one or more sensors in the fluid inlet path. By activating a splitting mode in such an embodiment, these requirements may be moderated to advantageously enable to extend an operating range of fluid flow values by exemplary embodiments.

The pump may be adapted to be controllable, for instance based on a flow rate in the second path measured by the second path sensor or based on any other criteria, so that a composition of the first fluidic component and the second fluidic component is at a target ratio. It is also possible that individual ones of the first inlet conduit, the second inlet conduit and/or optionally at least one of at least one further inlet conduit is controlled so that a fluid composition of different components at a position of a separation column matches with user-defined requirements, for instance fits to a gradient run.

A control or regulation capability for controlling or regulating a fluid flow characteristic may be included in one or more of different entities of the fluidic apparatus, for instance in the pump and/or in a variable restrictor and/or in one or more of the sensors and/or in a control unit. Criteria for such a control may be measured flow rates, a target fluid flow, a target fluid composition, etc.

In an embodiment, the system may be operated selectively in a split mode or in a splitless mode. In a split mode, the fluidic apparatus downstream the splitting point can be operated in such a manner that a definable ratio of the fluid is conducted in the waste path and the remainder is conducted into the use path. For instance, the fluidic apparatus may be adapted for being operable in the split mode when the flow rate is smaller than a predefined threshold value. For instance, the split mode may be adjusted when the flow rate is below 10 µl/min, for instance between about 0.1 µl/min and about 10 µl/min.

In a splitless mode, no splitting is performed (for instance by closing one or more of channels beginning at the splitting point) so that no fluid is lost by being conducted into the waste path. Such an embodiment may be advantageous when a relatively high flow rate is desired, for instance when the flow rate is above a predefined threshold value. In an embodiment, the splitless mode can be adjusted when the flow rate is above about 10 µl/min, for instance between about 10 µl/min and about 100 µl/min.

The pump may be adapted to be controllable based on a flow rate of the fluid measured by the inlet sensor. Hence, a regulation of the pumping channels based on a present flow rate may be possible. It is also possible that an operation mode of the pump is set based on a target flow defined by a measurement or by an operator. Particularly, the pump may be adapted to be controllable so that a flow rate in the second path is at a predefined target value. For instance, the system or a user may define a target value of a flow rate to be achieved. The pump can then be controlled to obtain exactly this flow rate. In an embodiment, it is possible that the pump receives flow rate readings from the inlet sensor and/or the second path sensor and adjusts its pumping performance (for instance pump rate) to a value which depends on the measured flows. In one embodiment, the pump actively picks up one or more flow rate readings from one or more of the sensors. In another embodiment, a control unit may pick up one or more flow rate readings from one or more of the sensors, may optionally pre-process corresponding sensor data, and may actively control the pump in accordance with the raw or pre-processed sensor data. Hence, the pump may act as an active self-controlled entity or as a passive entity being controllable by a control unit or even directly by the sensor or sensors.

In an embodiment, the second path sensor may be arranged in the second path downstream the splitting point and the first path may be free of a sensor. In such an embodiment, information regarding a flow rate in the first path may be obtained from the knowledge of the flow rate in the second path in combination with measurement results from the fluidic inlet path. However, in an alternative embodiment, a first path sensor may be additionally arranged in the first path as well. In an alternative embodiment, the second path sensor may be arranged in the second path downstream the splitting point and the first path may comprise an additional sensor which may be denoted as a first path sensor.

In an embodiment, a variable restrictor (for instance an adjustable valve, a variable spring loaded ball valve, etc.) may be arranged for instance in the first path, wherein a fluid flow through the variable restrictor may be adjustable (in a stepwise or continuous way) based on a flow rate of the part of the fluid conducted into the second path and measured by the second path sensor.

The opening degree of the variable restrictor may be adjustable so that a flow rate in the second path sensor is at a predefined target value. Therefore, a target value of a flow rate in the second path sensor may be defined by the system or by an operator, and the opening degree of the variable restrictor may then be controlled so that particularly this target value can be achieved.

The variable restrictor may be adjustable to be completely closed in a splitless operation mode so that the entire fluid flows through the second path. Thus, a splitless operation mode may coincide with a complete closure of the variable restrictor so that no fluid can pass through the variable restrictor into the first path. In such a scenario, all the fluid provided in the inlet fluidic path will be conducted into the second path for further use, particularly for sample separation procedures.

The fluidic apparatus may comprise a fluidic selector (such as a multiple port valve) being switchable to selectively enable or disable flow of the fluid into the first path. Such a fluidic selector may be a simple on/off switch, i.e. either allowing a certain quantity of fluid to flow through the fluidic selector into the first path or being closed to disable any fluid flow into the first path. However, in a more sophisticated embodiment, a more refined operation mode of the fluidic selector may be adjusted, allowing a user to precisely control the performance of the fluidic system.

The fluidic selector (for instance a switch) may be switched to a position to disable flow of the fluid into the first path. For instance, when the flow rate of the fluid becomes too low, the fluidic selector may prevent flow of fluid into the waste path, since the fluid is required in the use path.

The fluidic selector may be adapted to selectively enable flow of the fluid into the waste path according to a selectable one of a plurality of different first path enable modes. The channel can be blocked completely in a mode which may be denoted as a blank nut mode. One or more hydraulic resistor modes may be adjustable. A hydraulic resistor can be considered as a fluidic impedance, allowing a certain amount of fluid flowing into the waste path. A purge mode may correspond to a flushing of the corresponding channel.

The fluidic apparatus may comprise a single control unit adapted for controlling operation of both the second path sensor and the inlet sensor. Such a common processing unit (for instance a microprocessor or a central processing unit, CPU) may allow to correspondingly control the second path sensor downstream the splitting point as well as the inlet sensor upstream the splitting point. Such a control unit may also control pump/pumps and/or variable restrictor/fluidic selector based on measurement results of the sensor(s). Taking such a measure may allow for a central control of the system since both pump control upstream the splitting point as well as operation of a sample separation downstream the splitting point may be coordinated and synchronized. In an embodiment, the single control unit may use signals indicative of the flow rates and measured by the second path sensor and by the inlet sensor as input parameters and may calculate one or more control parameters for controlling different components of the fluidic apparatus based on these parameters.

In an embodiment, the fluidic path may comprise a substrate on and/or in which at least a part of the fluid inlet path, of the inlet sensor, of the splitting point, of the first path, of the second path and/or of the second path sensor may be integrated. Further components such as a separation column may be integrated on and/or in the substrate or chip as well. Such a substrate may be a plate, particularly a plate made of metal, a plastic, a ceramic, and/or a glass material. By taking this measure, the fluidic apparatus may be adapted as a chip-like device which allows for a sample separation with very small dimensions. Such an embodiment may be advantageous particularly when operating the fluidic apparatus with very small flow rates of 1 µl/min and less.

The fluidic apparatus may further comprise a third path (and optionally at least one further path) configured as a further use path (or as a further column path) adapted for guiding a part of the fluid towards the processing unit (for instance the sample separation unit) using the part of the fluid for the processing application, particularly for the sample separation application. A path selector may be adapted for selecting either the second path or the third path for guiding the part of the fluid towards the processing unit. In an embodiment, the second path may have a conduit (such as a fluidic channel) with a larger cross-section (that is a cross-section of a lumen through which a fluid may flow) than a cross-section of a conduit (that is a cross-section of a lumen through which a fluid may flow) of the third path. The path selector may be adapted for selecting the second path when a fluid flow is above a predefined threshold value (for example 1 µl/min) and for selecting the third path when the fluid flow is below the predefined threshold value.

In an embodiment, the fluidic apparatus may be configured to cover a very wide range of flow rates at an apparatus outlet (for instance at a position of a separation column). As the internal volume from the splitting point to the apparatus outlet may be flushed with the corresponding flow rate, it may be desired to keep the volume low. Otherwise the time to flush the volume may be too long for low flow rates, especially for flow rates smaller than 1 µl/min. Therefore, it may be an advantage to keep the cross section of the conduits sufficiently small.

On the other hand, the conduit between the splitting point and the apparatus outlet may generate a pressure drop as soon as a fluid is pumped through the conduit. This pressure drop may be dependent on fluid properties, flow rate of the fluid and the conduit geometry (for instance cross section and length). This pressure drop may be significantly high at bigger flow rates if the cross section of the conduit is too small.

It may be a further advantage of an embodiment of the fluidic apparatus to work with different conduits dependent on the total flow rate at the apparatus outlet. A first conduit may be designed to fulfill needs for flow rates below a predefined threshold value of for instance smaller than 1 µl/min (small cross section) and a second conduit may be designed for flow rates at or above the predefined threshold value of for instance above 1 µl/min (cross section bigger).

It may be a further advantage of an apparatus according to an exemplary embodiment with selectable outlet conduits, that the corresponding sensors elements can be identical. For flow sensors for example, the linear fluid velocity within the sensor element may be measured. By a different size of the cross section of the conduit within the sensor element the flow rate range of the sensor may be adaptable. This offers the possibility to use the same sensor design for different flow rate ranges. For instance 0.010 µl/min to 1 µl/min and 1 µl/min to 100 µl/min.

An appropriate fluidic selector may connect either conduit one or two dependent on the total flow rate request.

In an embodiment, separation columns with very small diameters or geometric dimensions may be implemented for liquid chromatography which requires small flow rates in the order of magnitude of microliters or nanoliters. This may correspond to very small flow rates of about 0.05 μl/min to about 100 μl/min. In this range of very small flow rates, it may be conventionally difficult to scale pumps. Exemplary embodiments combine two features in a synergetic manner, namely the provision of a sensor upstream a splitting point for pump control purpose with a sensor downstream the splitting point for adjusting a splitting ratio. A variable restrictor downstream the splitting point may be controlled based on a measured flow rate so that a flow towards a separation column, for instance an HPLC, may be kept constant. Channels in the fluid inlet path may consequently work at higher flow rates which are reliably pumpable by a pump. Furthermore, a working flow may be controlled (thereby for instance indirectly controlling a waste flow) so as to achieve in total a desired flow rate. Therefore, a fluidic apparatus according to an exemplary embodiment is capable to operate with multiple channels at a comfortably high flow rate as compared to a conventional splitting free fluidic apparatus or pump. Advantageously, a pump of such a fluidic apparatus can be controlled based on detection signals of a sensor upstream of a splitting point. A pump can be operated at a small flow rate, and can work in a robust and reliable manner, so that control measurements may be performed in an early portion of the flow path. Such a concept may allow to implement simple sensors, for instance sensors having a small dynamic range, without losing performance.

Embodiments may further allow to safe waste flow in a splitless mode and reduce waste flow to a minimum in split mode, for instance in case of expensive fluids (for instance expensive solvents in liquid chromatography). Furthermore, a sensor can be implemented in supply channels and in a column path so that a dead volume between a mixing point and a flow sensor may be estimated and a downstream sensor may be calibrated. Such a system is also robust against leakage since it may allow to detect and compensate for a leak.

The system may comprise a processing element filled with a separating material. Such a separating material which may also be denoted as a stationary phase may be any material which allows an adjustable degree of interaction with a sample so as to be capable of separating different components of such a sample. The separating material may be a liquid chromatography column filling material or packing material comprising at least one of the group consisting of polystyrene, zeolite, polyvinylalcohol, polytetrafluorethylene, glass, polymeric powder, silicon dioxide, and silica gel, or any of above with chemically modified (coated, capped etc) surface. However, any packing material can be used which has material properties allowing an analyte passing through this material to be separated into different components, for instance due to different kinds of interactions or affinities between the packing material and fractions of the analyte.

At least a part of the processing element may be filled with a fluid separating material, wherein the fluid separating material may comprise beads having a size in the range of essentially 1 μm to essentially 50 μm. Thus, these beads may be small particles which may be filled inside the separation section of the fluidic apparatus. The beads may have pores having a size in the range of essentially 0.01 μm to essentially 0.2 μm. The fluidic sample may be passed through the pores, wherein an interaction may occur between the fluidic sample and the pores.

The fluidic apparatus may be adapted as a fluid separation system for separating components of the sample. When a mobile phase including a fluidic sample passes through the fluidic apparatus, for instance with a high pressure, the interaction between a filling of the column and the fluidic sample may allow for separating different components of the sample, as performed in a liquid chromatography device.

However, the fluidic apparatus may also be adapted as a fluid purification system for purifying the fluidic sample. By spatially separating different fractions of the fluidic sample, a multi-component sample may be purified, for instance a protein solution. When a protein solution has been prepared in a biochemical lab, it may still comprise a plurality of components. If, for instance, only a single protein of this multi-component liquid is of interest, the sample may be forced to pass the columns. Due to the different interaction of the different protein fractions with the filling of the column (for instance using a gel electrophoresis device or a liquid chromatography device), the different samples may be distinguished, and one sample or band of material may be selectively isolated as a purified sample.

The fluidic apparatus may be adapted to analyze at least one physical, chemical and/or biological parameter of at least one component of the mobile phase. The term "physical parameter" may particularly denote a size or a temperature of the fluid. The term "chemical parameter" may particularly denote a concentration of a fraction of the analyte, an affinity parameter, or the like. The term "biological parameter" may particularly denote a concentration of a protein, a gene or the like in a biochemical solution, a biological activity of a component, etc.

The fluidic apparatus may be implemented in different technical environments, like a sensor device, a test device, a device for chemical, biological and/or pharmaceutical analysis, a capillary electrophoresis device, a liquid chromatography device, a gas chromatography device, an electronic measurement device, or a mass spectroscopy device. Particularly, the fluidic apparatus may be a High Performance Liquid device (HPLC) by which different fractions of an analyte may be separated, examined and analyzed.

The processing element may be a chromatographic column for separating components of the fluidic sample. Therefore, exemplary embodiments may be particularly implemented in the context of a liquid chromatography apparatus.

The fluidic apparatus may be adapted to conduct a liquid mobile phase through the processing element and optionally a further processing element. As an alternative to a liquid mobile phase, a gaseous mobile phase or a mobile phase including solid particles may be processed using the fluidic apparatus. Also materials being mixtures of different phases (solid, liquid, gaseous) may be processed using exemplary embodiments.

The fluidic apparatus may be adapted to conduct the mobile phase through the system with a high pressure, particularly of at least 5.000 psi more particularly of at least 10.000 psi.

The fluidic apparatus may be adapted as a microfluidic apparatus. The term "microfluidic apparatus" may particularly denote a fluidic apparatus as described herein which allows to convey fluid through microchannels having a dimension in the order of magnitude of less than 500 μm, particularly less than 200 μm, more particularly less than 100 μm or less than 50 μm or less. The fluidic apparatus may also be adapted as a nanofluidic apparatus. The term "nanofluidic apparatus" may particularly denote a fluidic apparatus as described herein which allows to convey fluid through nanochannels having even smaller dimensions than the microchannels.

At least one of the group consisting of the inlet sensor and the second path sensor may comprise at least one of the group consisting of a flowmeter and a pressure sensor. In other words, any sensor mentioned herein may be realized, for instance as a flowsensor or as a pressure sensor or by any other sensor capable of estimating, directly or indirectly, a flow rate.

BRIEF DESCRIPTION OF DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

The illustration in the drawing is schematically.

Exemplary embodiments provide an apparatus for and a process of preparing volume flows of liquids for a chromatographic column. Such embodiments are related to generate stable and precise flow rates for liquid chromatography and may be especially useful for flow rates in the range of a few µl/min or even nl/min as may be needed for some applications in the field of capillary and nano flow chromatography.

In the following, some basic recognitions of the present invention will be explained based on which exemplary embodiments of the invention have been developed.

In the field of capillary and nano HPLC it may be desired to deliver solvents at a very low flow rate in the range of several µl/min down to 50 nl/min or less. Comparable to standard or normal bore chromatography it may be further desired to deliver these low flow rates in a mixture of at least two solvents which are to be mixed continuously and the composition of the resulting mixed fluid may be changed over time.

Conventionally, low flow systems may be based on so-called passive splitter technology. The pump operates at quite high flow rates. Typically, these flow rates are in the range of several 100 µl/min. At the pump outlet, the delivered flow rate can be divided into a working flow and a waste flow by simply adding restrictors in the working and in the waste path such that the ratio of the restrictions determines the flow rate in the working path. The output flow rate is not controlled and may therefore be not reliable and robust.

Conventionally, there are two different technical concepts to solve the problem of delivering stable low flow rates, an active split system and a direct delivery of solvent.

In an active split system, a pump is delivering the solvent at a higher flow rate than needed for the chromatography, similar to the passive split system. However, at a pump outlet the column flow rate is measured and monitored for instance by a flow sensor device. The split ratio is controlled such that the column flow rate is constant independent from restriction in the column flow path. Such systems have a very high performance in respect of flow reproducibility and composition stability, because the pump syringes operate at a convenient flow rate and any kind of flow fluctuation in the individual channels has lower influence on performance. Under undesired circumstances, the total delivered amount of solvent may be significant more than the amount needed for chromatographic purposes resulting in a very high solvent waste. A further disadvantage is the reliability of the fluidic composition in case more fluids are delivered and mixed.

In another conventional approach, a so-called direct delivery mode, the nano flow rates are delivered without any splitting. The delivered flow rate in each individual channels of the pump is measured by a flow sensor and controlled. A challenge of this approach are the extremely low flow rates which are required for nano flow applications. Because of composition out of typically two solvents each channel has to be able to deliver 1% of the lowest total flow rate. On the other hand each pump channel should be able to deliver 100% of the highest flow rate. As compared to the split approach, the dynamic need of the sensor element is 100-fold higher.

In the following, referring to FIG. 1, a fluidic apparatus 100 according to an exemplary embodiment will be explained.

Figure 1:
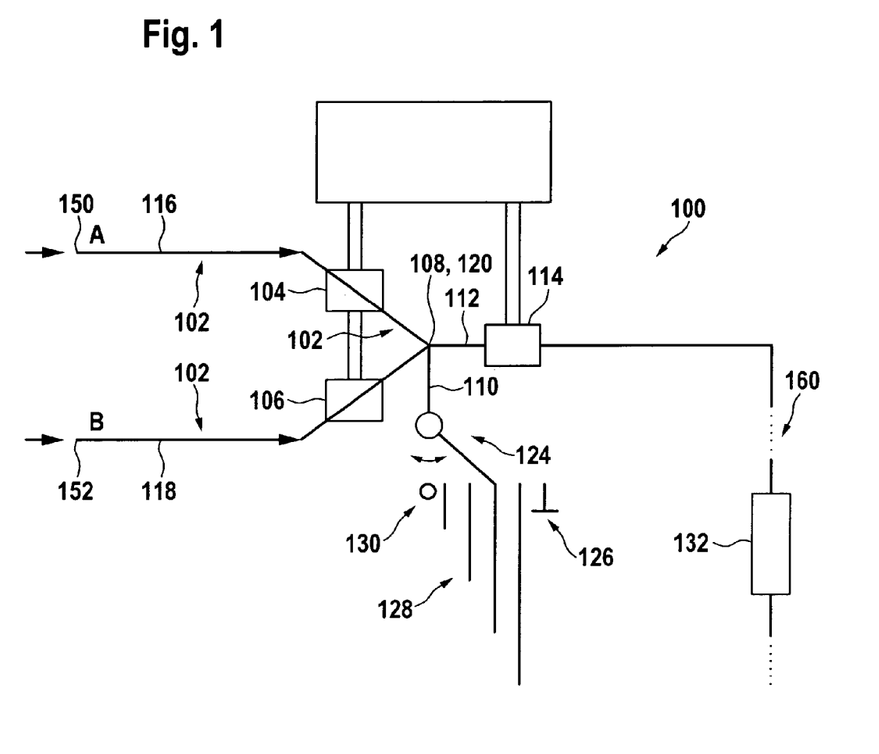
FIG. 1 illustrates a fluidic apparatus according to an exemplary embodiment.

The fluidic apparatus 100 shown in FIG. 1 is part of a sample separation system, more particularly of a liquid chromatography sample separation system which involves mixture of different solvents and concentrations which may vary over time. This can be achieved with the fluidic apparatus 100 in a very precise and reliable manner.

The fluidic apparatus 100 comprises a fluid inlet path 102 for supplying different components of a fluid. A first inlet port 150 is adapted for providing a first fluid A such as water pumped by a pump (not shown in FIG. 1) from a vial or fluid container. Via a second fluid inlet port 152, another component B of a multi-component fluid may be provided, for instance an organic solvent such as acetonitrile, ACN.

The fluid inlet path 102 comprises a first inlet sensor 104 (such as a flowmeter) capable of measuring a flow rate of water pumped into the system 100 via the first fluid input port 150, and comprises a second inlet sensor 106 (such as a flowmeter) adapted for measuring a flow rate of the second composition of the mixture to be produced, namely the organic solvent acetonitrile. Each of the first and the second inlet sensors 104, 106 is adapted for measuring a flow rate of the corresponding fluid in corresponding fluid conduits 116 and 118, respectively, of the fluid inlet path 102.

At a mixing point 120, the first fluid supplied via the first fluid conduit 116 and the second fluid supplied via the second fluid conduit 118 are mixed to form a mixture in accordance with the individual flow rates of the two different fluids. In the shown embodiment, the mixing point 120 is integrally formed with a splitting point 108 arranged downstream the fluid inlet path 102 and being adapted for splitting the fluid composition A+B into sub-volumes conducted into a first path 110 and into a second path 112.

A second path sensor 114 (such as a flowmeter) is arranged within the second path 112 and is adapted for measuring a flow rate of a part of the fluid conducted from the splitting point 108 into the second path 112. Another part of the fluid is conducted into the first path 110. Since the fluid being conducted through the path 110 may be conducted towards a waste, the first path 110 may also be denoted as a waste path. Since the part of the fluid conducted through the second path 112 will later be used for sample separation purposes, the second path 112 may also be denoted as a column path or a use path.

As can be taken from FIG. 1, the fluid guided through the second path 112 and through the second path sensor 114 is then further conducted towards a chromatographic column 132 for separating different components of a sample being denoted with reference numeral 160 and being brought in interaction with separation material of the chromatographic column 132 and the mobile phase formed by the fluid A+B originating from the inlet ports 150, 152.

The first inlet sensor 104 is adapted for measuring a flow rate of the first fluidic component A of the fluid being conducted within the fluidic conduit 116. The second inlet sensor 106 is adapted for measuring a flow rate of the second fluidic component B of the fluid being conducted within the fluidic conduit 118. The second path sensor 114 is adapted for measuring a flow rate of the fluidic composition A+B in the second fluidic channel 112.

A ratio between the flow rate of the first fluidic component A and the flow rate of the second fluidic component B can be adjusted for adjusting a composition of the fluid. For releasing different fractions of the sample 160 trapped on the liquid chromatography column 132, the relative concentration of water and organic solvent are to be changed for running a gradient mode. For this purpose, a common control unit 134 controlling operation of the sensors 104, 106 and 114 and receiving measurement signals from the sensors 104, 106 and 114 can be used for correspondingly operating pumps (not shown) pumping fluidic components A and B, respectively, through channels 116 and 118, respectively. The pumps define, with their operation power, a flow of the fluid supplied via the inlet ports 150 and 152, respectively. The pumps can be controlled by the common control unit 134 based on flow rates measured by the inlet sensors 104 and 106. The pumps may be controlled in such a manner that a total flow rate of the fluid in the second path sensor 114 is at the predefined target value.

The fluidic apparatus 100 further comprises a fluidic selector 124 which is switchable (for instance under control of the control unit 134 or by a user) to selectively enable or disable flow of the fluid into the first path 110. In the operation mode shown in FIG. 1, there is a fluid communication between the first path 110 and one of four restrictor lines 128. Different restrictor lines 128 correspond to different fluidic impedances and therefore to different splitting ratios of fluid between lines 110 and 112. Other operation modes settable via the fluidic selector 124 are a purge mode 130 (rinsing line 110) or a blank nut mode 126 (blocking line 110). Thus, a highly flexible system is provided which not only allows to change between a split mode and a splitless mode, but which also allows to adjust one of several different split modes.

In the embodiment of FIG. 1, the second path sensor 114 may be a flow sensor for nano flow rates of for instance 0.01 μl/min to 1 μl/min (or of for instance 0.05 μl/min to 5 μl/min). In contrast to this, the channel flow rate sensors 104, 106 may be adapted for measuring in a higher range, for instance in a flow rate range between 100 nl/min and 10 μl/min.

Figure 2:
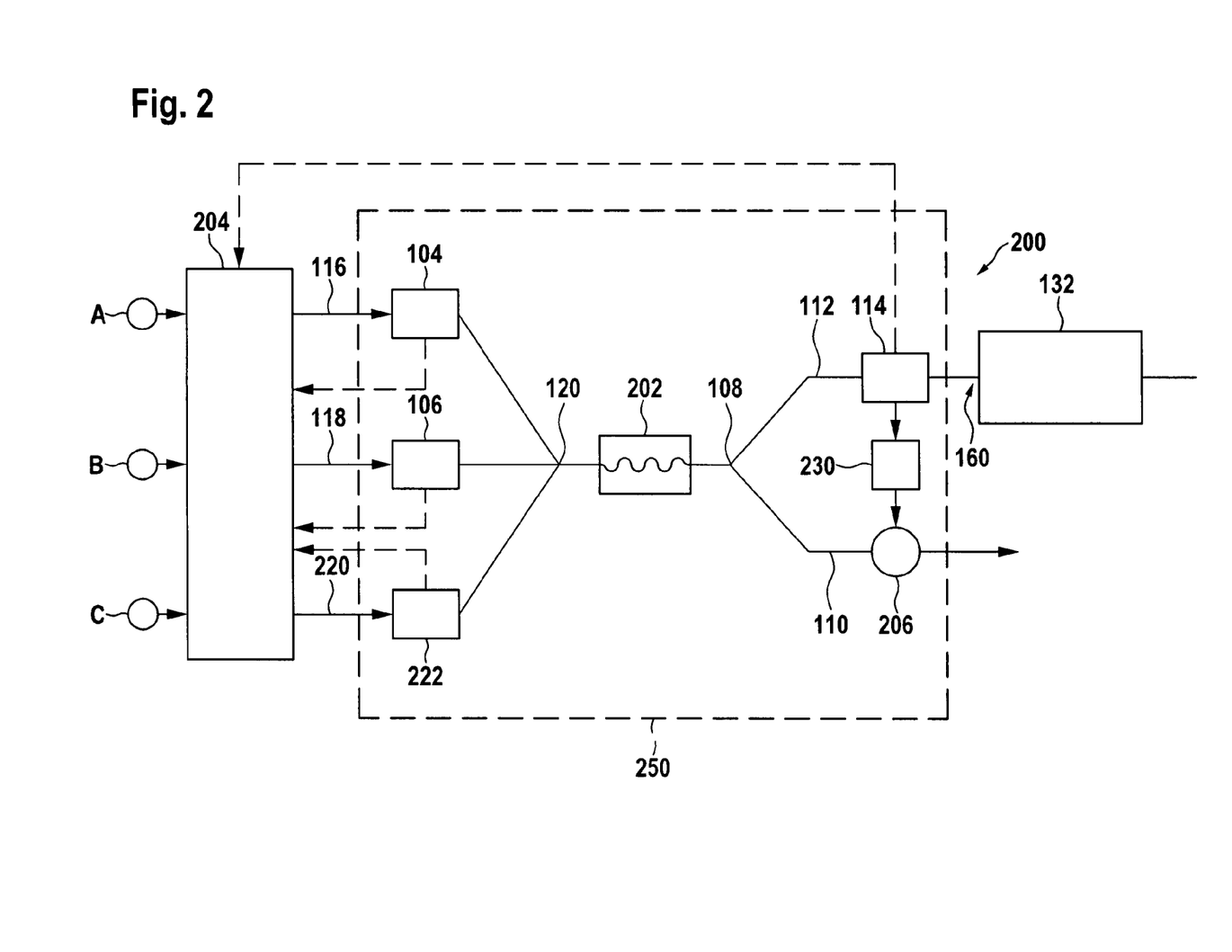
FIG. 2 illustrates a fluidic apparatus according to another exemplary embodiment.

FIG. 2 shows a fluidic apparatus 200 according to another exemplary embodiment.

In this embodiment, three different fluids relating to channels A, B and C can be pumped by pumps 204 towards a mixing point 120. Before reaching the mixing point 120, the flow of the corresponding fluids in fluidic channels 116, 118, 220 are individually measured by channel flow rate sensors 104, 106, 222. As can be taken from FIG. 2, the measurement signals measured by the channel flow rate sensors 104, 106, 222 are fed back to the pumps 204 to control the pumps 204 correspondingly. It is also possible that a measurement signal measured by the column path flow rate sensor 114 is fed back to the pumps 204 to control the pumps 204 correspondingly.

In the embodiment of FIG. 2, a dedicated mixing unit 202 with a curved fluidic channel is provided between the initial mixing point 120 and a splitting point 108. The mixing unit 202 is adapted for selectively promoting mixture of the fluidic components A, B and C. After being split into two different portions at splitting point 108, the two fluids flow through a use path 112 and through a waste path 110, respectively. The flow rate in the use path is measured by the use path sensor 114. Based on the measured flow rate, a processing unit 230 may calculate or compute a specific control signal for controlling a fluidic variable restrictor 206. In accordance with the control signal, and hence in accordance with the flow rate measured by the sensor 114, a hydraulic restriction for the variable restrictor 206 may be adjusted. Thus, a portion of the fluid split at the splitting point 108 between the conduits 110, 112 may be adjusted. The remainder of the fluid which is not supplied through channel 110 flows through the channel 112. This allows to indirectly adjust the flow rate of the fluid in the use path 112 which can then be brought in interaction with the sample 160 to be separated in a liquid chromatography column 132.

Figure 3:
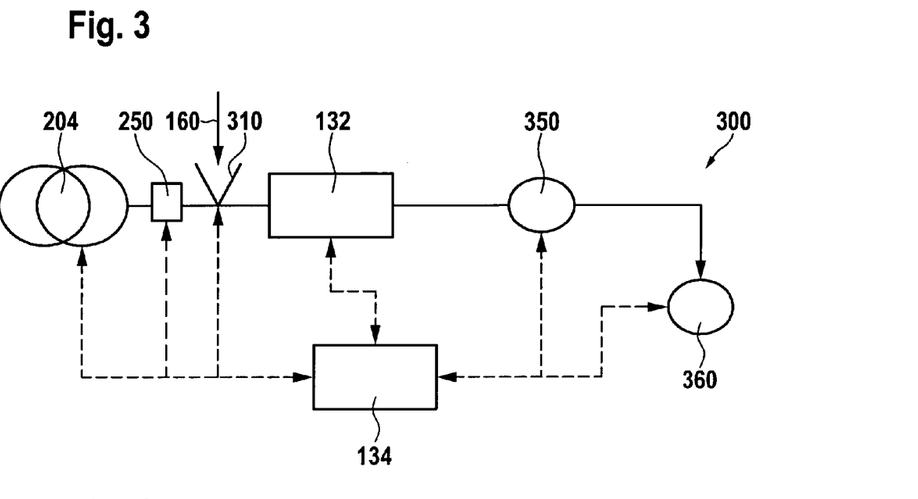
FIG. 3 illustrates a HPLC according to an exemplary embodiment.

FIG. 3 depicts a general schematic of a liquid separation system 300 according to an exemplary embodiment.

A pump 204—as a mobile phase drive—drives a mobile phase through a separating device 132 (such as a chromatographic column) comprising a stationary phase. A sampling unit 310 can be provided between the pump 204 and the separating device 132 in order to introduce a sample fluid 160 to the mobile phase. The stationary phase of the separating device 132 is adapted for separating compounds of the sample liquid 160. A fluidic mixing and splitting path 250, as the one shown in FIG. 2, is provided for controlling quantities of a fluid introduced into the liquid separation system 300. A fractionating unit 360 can be provided for outputting separated compounds of sample fluid. A control unit 134 centrally controls operation of the liquid separation system 300. The separated sample can be detected in e.g. a fluorescence detector 350.

Figure 4:
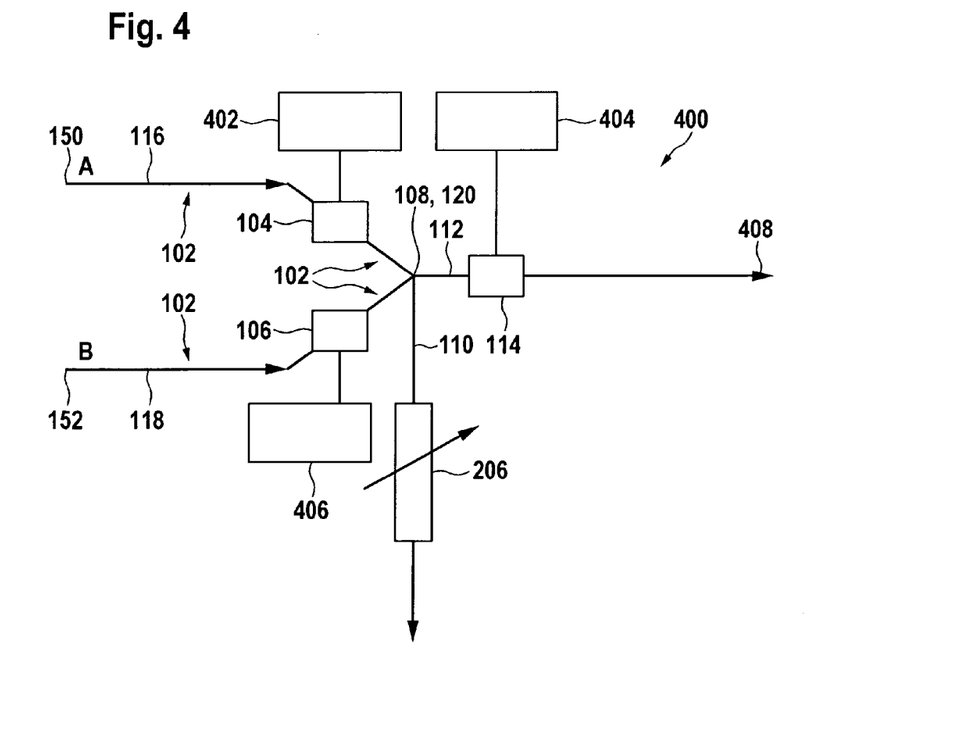
FIG. 4 to FIG. 7 each illustrates a different configuration of fluidic apparatuses according to exemplary embodiments.

FIG. 4 shows a fluidic apparatus 400 according to an exemplary embodiment.

The fluidic apparatus 400 has a variable resistor 206. Flow sensor 104 has an assigned sensor electronics unit 402, flow sensor 106 has an assigned sensor electronics unit 406, and flow sensor 114 has an assigned sensor electronics unit 404. A fluidic outlet is denoted with reference numeral 408.

Figure 5:
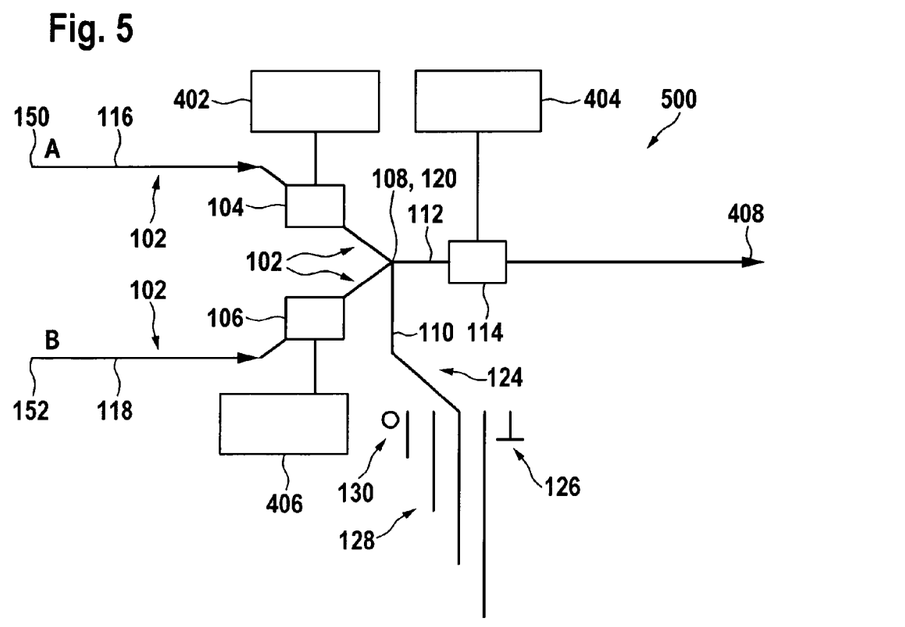

FIG. 5 shows a fluidic apparatus 500 according to an exemplary embodiment.

The fluidic apparatus 500 has a selectable flow resistor 124.

Figure 6:
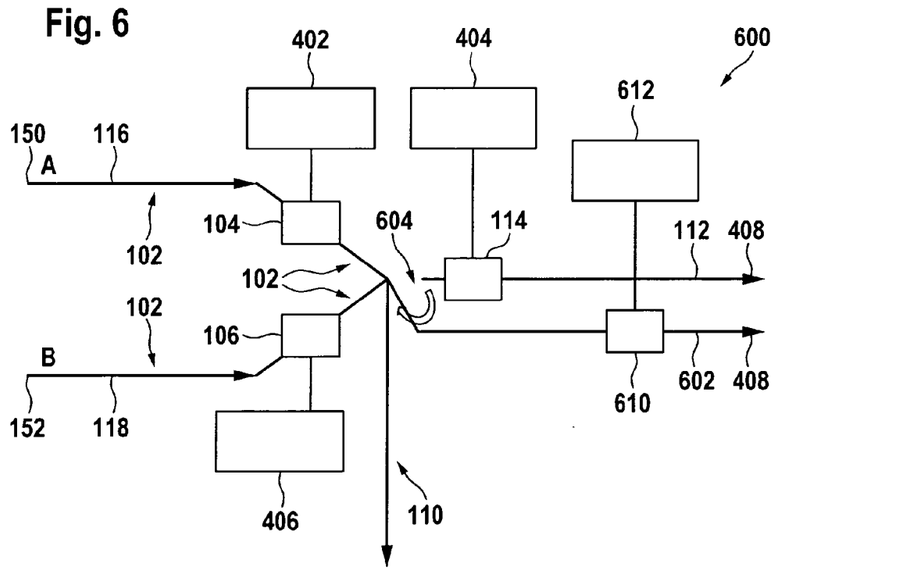

FIG. 6 shows a fluidic apparatus 600 according to an exemplary embodiment. The fluidic apparatus 600 has two different outlet conduits 112 and 602. Particularly, an additional third path 602 is provided and configured as a further use path adapted for guiding fluid towards fluid outlet 408. A path selector 604 is provided and adapted for selecting, at a time, only one of the second path 112 and the third path 602 for guiding the part of the fluid towards the fluid outlet 408. The second path 112 has a conduit with a larger cross-section than a cross-section of a conduit of the third path 602. The path selector 604 is adapted for selecting the second path 112 when a fluid flow is above a predefined threshold value and for selecting the third path 602 when the fluid flow is below the predefined threshold value. A third path sensor 610 (such as a flowmeter) is arranged in the third path 602 to measure a flow there. Third path sensor 610 can be controlled and/or read out by a separate sensor electronic block 612.

Figure 7:
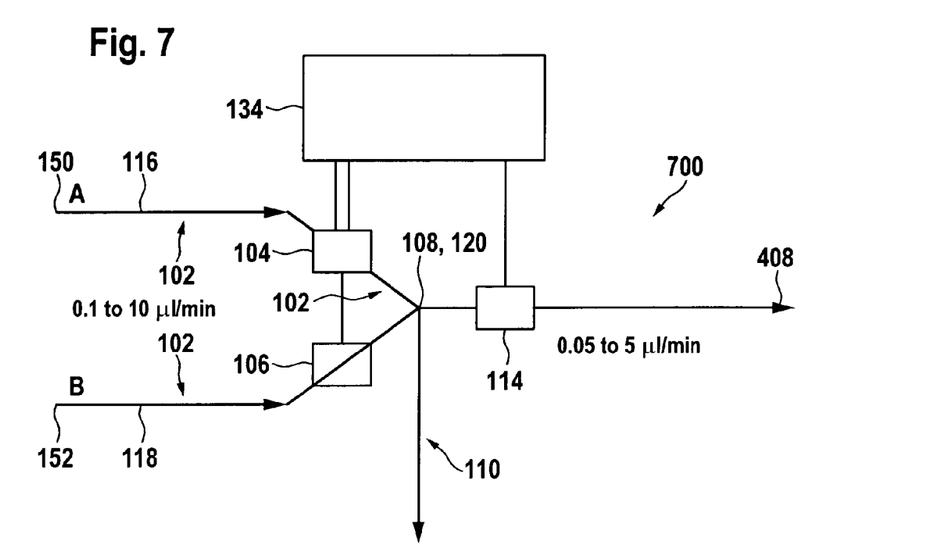

FIG. 7 shows a fluidic apparatus 700 according to an exemplary embodiment.

The fluidic apparatus 700 has a combined electronic and controller 134 for controlling the fluidic apparatus 700.

In the following, referring to FIG. 8, a fluidic apparatus 800 according to an exemplary embodiment will be explained.

Figure 8:
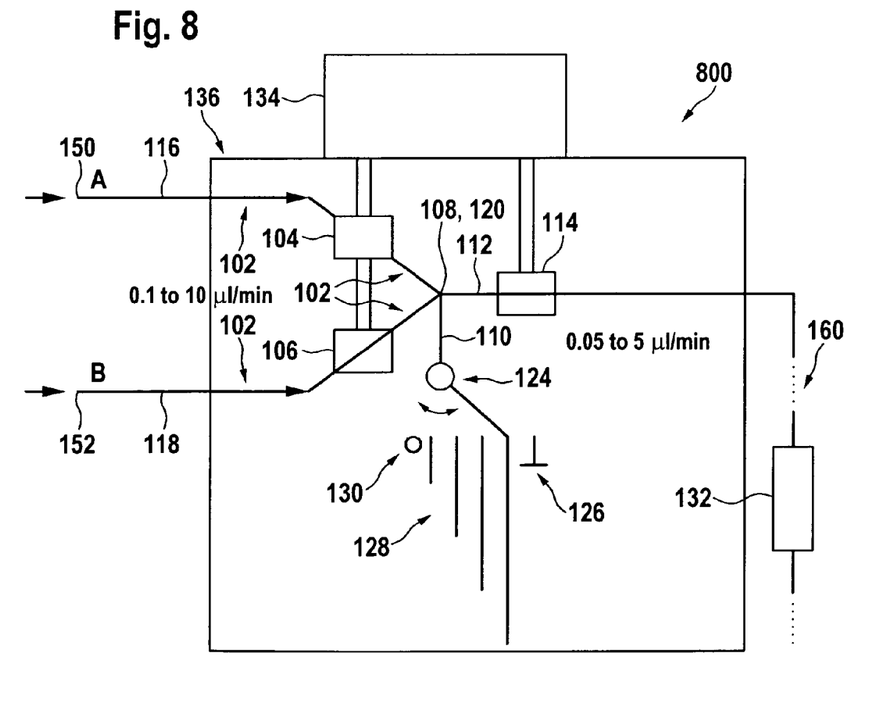
FIG. 8 illustrates a fluidic apparatus according to another exemplary embodiment.

As can be taken from FIG. 8, fluidic apparatus 800 differs from fluidic apparatus 100 in that several ones the described components may are integrated with a metal plate 136 serving

The invention claimed is:

1. A fluidic apparatus for a sample separation system, the fluidic apparatus comprising
   a fluid inlet path for supplying a fluid,
   an inlet sensor adapted for measuring a flow rate of the fluid in the fluid inlet path,
   a splitting point arranged downstream from the fluid inlet path and adapted for splitting the fluid into a first path and into a second path, and
   a second path sensor adapted for measuring a flow rate of a part of the fluid conducted into the second path,
   wherein the fluid inlet path comprises a first inlet conduit for supplying a first fluidic component of the fluid, a second inlet conduit for supplying a second fluidic component of the fluid, and a mixing point for mixing the first fluidic component with the second fluidic component upstream from the splitting point.

2. The fluidic apparatus according to claim 1, comprising at least one of:
   the first path is a waste path adapted for guiding a part of the fluid towards a waste;
   the second path is a use path adapted for guiding a part of the fluid towards a processing unit, using the part of the fluid for a processing application;
   the second path is a use path adapted for guiding a part of the fluid toward a sample separation unit, using the part of the fluid for a sample separation application;
   the second path sensor is arranged in the second path.

3. The fluidic apparatus according to claim 1, comprising at least one of:
   the inlet sensor is adapted for measuring a flow rate of at least one of the first fluidic component and the second fluidic component of the fluid in the second inlet conduit;
   a ratio between the flow rate of the first fluidic component in the first inlet conduit and the flow rate of the second fluidic component in the second inlet conduit is adjustable for adjusting a composition of the fluid;
   a ratio between the flow rate of the first fluidic component in the first inlet conduit and the flow rate of the second fluidic component in the second inlet conduit is adjustable for adjusting a time-dependent composition of the fluid;
   a mixing unit arranged upstream the splitting point and being adapted for promoting mixture of the first fluidic component and the second fluidic component.

4. The fluidic apparatus according to claim 1,
   comprising a pump in the fluid inlet path for pumping the fluid through the fluidic apparatus.

5. The fluidic apparatus according to claim 4, comprising at least one of:
   the pump is adapted for pumping the fluid through the second flow path towards a sample separation unit with a flow rate in the second flow path in a range between 0.01 μl/min and 500 μl/min; the pump is adapted for pumping the fluid through the second flow path towards a sample separation unit with a flow rate in the second flow path in a range between 0.05 μl/min and 100 μl/min;
   the pump is adapted to be controllable based on a flow rate measured by the inlet sensor;
   the pump is adapted to be controllable so that a flow rate in the second path sensor is at a predefined target value;
   the pump is adapted to be controllable, particularly based on a flow rate in the second path measured by the second path sensor, so that a composition of the first fluidic component and the second fluidic component is at a target ratio.

6. The fluidic apparatus according to claim 1, comprising a variable restrictor arranged in the first path, wherein a fluid flow through the variable restrictor is adjustable based on a flow rate of the part of the fluid conducted into the second path and measured by the second path sensor.

7. The fluidic apparatus according to claim 6, comprising at least one of:
   the variable restrictor is adjustable so that a flow rate in the second path sensor is at a predefined target value;
   the variable restrictor is adjustable to be completely closed in a splitless operation mode in which the fluid flows entirely through the second path.

8. The fluidic apparatus according to claim 1,
   comprising a fluidic selector being switchable to selectively enable or disable flow of the fluid into the first path.

9. The fluidic apparatus according to claim 8, comprising at least one of:
   the fluidic selector is switchable to disable flow of the fluid into the first path when a flow rate of the fluid is below a threshold flow value;
   the fluidic selector is adapted to selectively enable flow of the fluid into the first path according to a selectable one of a plurality of different first path enable modes, wherein the first path enable modes comprise at least one of the group consisting of a blank nut mode, one or more hydraulic restrictor modes, and a purge mode.

10. The fluidic apparatus according to claim 1,
    comprising a control unit adapted for controlling operation of the fluidic apparatus based on flow rates measured by the second path sensor and by the inlet sensor.

11. The fluidic apparatus according to claim 10, comprising at least one of:
    the control unit is adapted for controlling operation of both the second path sensor and the inlet sensor;
    the control unit is adapted for controlling operation of at least one of the group consisting of the pump, the variable restrictor, and the fluidic selector.

12. The fluidic apparatus according to claim 1,
    comprising a substrate on and/or in which at least a part of the fluid inlet path, the inlet sensor, the splitting point, at least a part of the first path, at least a part of the second path and the second path sensor are integrated,
    wherein the substrate comprises a plate.

13. The fluidic apparatus according to claim 1, wherein the second path is a use path adapted for guiding a part of the fluid towards a processing unit, using the part of the fluid for a processing application,
    the fluidic apparatus further comprising:
    a third path configured as a further use path adapted for guiding a part of the fluid towards the processing unit, using the part of the fluid for the processing application; and
    a path selector adapted for selecting one of the second path and the third path for guiding the part of the fluid towards the processing unit.

14. The fluidic apparatus according to claim 1, comprising at least one of:
- at least one of the group consisting of the inlet sensor and the second path sensor comprises at least one of the group consisting of a flowmeter and a pressure sensor;
- the fluidic apparatus is adapted so that the part of the fluid conducted into the second path is used for separation of a sample, particularly is conducted towards a sample separation unit for separation of a sample using the fluid;
- the fluidic apparatus is adapted as a fluidic chip device;
- the fluidic apparatus is adapted for separating compounds of a sample;
- the fluidic apparatus is adapted for purifying a sample;
- the fluidic apparatus is adapted to analyze at least one physical, chemical and/or biological parameter of at least one compound of a sample;
- the fluidic apparatus comprises at least one of the group consisting of a sensor device, a test device for testing a device under test or a substance, a device for chemical, biological and/or pharmaceutical analysis, a capillary electrophoresis device, a liquid chromatography device, an HPLC device, a gas chromatography device, a gel electrophoresis device, an electronic measurement device, and a mass spectroscopy device;
- the fluidic apparatus is adapted to conduct the fluid with a high pressure;
- the fluidic apparatus is adapted to conduct the fluid with a pressure of at least 100 bar, particularly of at least 500 bar, more particularly of at least 1000 bar;
- the fluidic apparatus is adapted to conduct a liquid fluid;
- the fluidic apparatus is adapted as a microfluidic apparatus;
- the fluidic apparatus is adapted as a nanofluidic apparatus;
- a processing element arranged downstream the second path and adapted for interacting with the fluid, wherein the processing element comprises a chromatographic column for separating components of a sample.

15. A method of handling a fluid in a sample separation system, the method comprising
- supplying the fluid to a fluid inlet path comprised of a first inlet conduit for supplying a first fluidic component of the fluid and a second inlet conduit for supplying a second fluidic component of the fluid,
- mixing the first fluidic component with the second fluidic component, measuring a flow rate of the fluid in the fluid inlet path;
- splitting the fluid downstream the fluid inlet path into a first path and into a second path; and
- measuring a flow rate of a part of the fluid conducted into the second path.

16. The fluidic apparatus according to claim 1, wherein the substrate comprises a plate made of one of the group consisting of a metal, a plastic, a ceramic, and glass.

17. The fluidic apparatus according to claim 1, wherein the second path is a use path adapted for guiding a part of the fluid toward a sample separation unit, using the part of the fluid for a sample separation application,
the fluidic apparatus further comprising:
- a third path configured as a further use path adapted for guiding a part of the fluid towards the sample separation unit, using the part of the fluid for the sample separation application; and
- a path selector adapted for selecting one of the second path and the third path for guiding the part of the fluid towards the processing unit.

* * * * *